(12) United States Patent
Aga et al.

(10) Patent No.: US 9,214,196 B2
(45) Date of Patent: Dec. 15, 2015

(54) SYSTEM AND METHOD FOR POWERING A WIRELESS SENSOR DEVICE

(75) Inventors: Arshan Aga, Mountain View, CA (US); Yun Yang, Los Altos, CA (US)

(73) Assignee: VITAL CONNECT, INC., Campbell, CA (US)

( * ) Notice: Subject to any disclaimer, the term of this patent is extended or adjusted under 35 U.S.C. 154(b) by 974 days.

(21) Appl. No.: 13/398,734

(22) Filed: Feb. 16, 2012

(65) Prior Publication Data

US 2013/0214850 A1 Aug. 22, 2013

(51) Int. Cl.
*G11C 5/14* (2006.01)
*A61B 5/00* (2006.01)
*G08B 29/18* (2006.01)
*G08B 21/04* (2006.01)

(52) U.S. Cl.
CPC ... *G11C 5/14* (2013.01); *A61B 5/00* (2013.01); *G08B 29/181* (2013.01); *A61B 5/0024* (2013.01); *A61B 5/6804* (2013.01); *G08B 21/0446* (2013.01)

(58) Field of Classification Search
None
See application file for complete search history.

(56) References Cited

U.S. PATENT DOCUMENTS

| | | | |
|---|---|---|---|
| 5,350,412 A * | 9/1994 | Hoegnelid et al. | 607/34 |
| 5,370,666 A * | 12/1994 | Lindberg et al. | 607/16 |
| 6,580,942 B1 * | 6/2003 | Willshire | 600/509 |
| 6,624,685 B2 | 9/2003 | Shih et al. | |
| 6,629,931 B1 * | 10/2003 | Begemann et al. | 600/508 |
| 7,483,734 B2 * | 1/2009 | Colthurst | 600/547 |
| 2001/0044318 A1 | 11/2001 | Mantyjarvi et al. | |
| 2003/0149349 A1 * | 8/2003 | Jensen | 600/372 |
| 2005/0043594 A1 * | 2/2005 | Dinsmoor et al. | 600/300 |
| 2006/0122540 A1 | 6/2006 | Zhu et al. | |
| 2008/0080705 A1 | 4/2008 | Gerhardt et al. | |
| 2009/0076336 A1 * | 3/2009 | Mazar et al. | 600/300 |
| 2009/0157141 A1 | 6/2009 | Chiao et al. | |
| 2010/0049028 A1 | 2/2010 | Shin et al. | |
| 2012/0035687 A1 * | 2/2012 | Lu et al. | 607/61 |

OTHER PUBLICATIONS

PCT International Search Report and Written Opinion of the International Searching Authority, issued May 21, 2013, application No. PCT/US2013/025603.

* cited by examiner

*Primary Examiner* — Rexford Barnie
*Assistant Examiner* — David Shiao
(74) *Attorney, Agent, or Firm* — Sawyer Law Group, P.C.

(57) ABSTRACT

A system and method for powering a wireless sensor device are disclosed. In a first aspect, the wireless sensor device comprises at least two electrodes configured to be attached to a body and at least two leads coupled to the at least two electrodes. The wireless sensor device also includes a system on chip (SoC) coupled to the at least two leads and a portable power source ($V_{batt}$) coupled to the SoC. When the at least two electrodes are attached to the body, a difference in resistance is measured between the at least two leads by the SoC and the difference in resistance is utilized by the SoC to enable the portable power source to activate the wireless sensor device.

16 Claims, 7 Drawing Sheets

SYSTEM AND METHOD FOR POWERING A WIRELESS SENSOR DEVICE

FIELD OF THE INVENTION

The present invention relates generally to wireless sensor devices, and more particularly, to a system and method for powering these wireless sensor devices.

BACKGROUND

There are wearable sensor devices that are worn by a user in a variety of applications. Hereinafter, these devices will be referred to as wireless sensor devices. Wireless sensor devices are available for a variety of applications including but not limited to behavioral modeling, electronic textiles, and health care monitoring systems. In many of these applications, the wireless sensor devices are attached directly to the user's skin to measure certain data.

As a result, these wireless sensor devices must be powered efficiently to ensure no gaps in the measurement of the data occur. Wireless sensor devices must also be powered innocuously to ensure the device does not become too bulky for the user to wear. Wireless sensor devices can be powered by portable power sources including but not limited to a rechargeable battery and solar cells. However, these types of portable power sources can lose power quickly over time. Oftentimes, recharging techniques may be used to extend the life of the portable power sources but to use such techniques adds cost and expense to the wireless sensor devices.

These issues limit the adoption of wireless sensor devices to select cases. Thus, for the majority of individuals requiring wireless sensor devices, there is a strong need for a non-invasive powering solution that overcomes the above issues. The present invention addresses such a need.

SUMMARY OF THE INVENTION

A system and method for powering a wireless sensor device are disclosed. In a first aspect, the wireless sensor device comprises at least two electrodes configured to be attached to a body and at least two leads coupled to the at least two electrodes. The wireless sensor device also includes a system on chip (SoC) coupled to the at least two leads and a portable power source ($V_{batt}$) coupled to the SoC. When the at least two electrodes are attached to the body, a difference in resistance is measured between the at least two leads by the SoC and the difference in resistance is utilized by the SoC to enable the portable power source to activate the wireless sensor device.

In a second aspect, the method comprises attaching at least two electrodes to a body and coupling at least two leads to the at least two electrodes. The method includes coupling a system on chip (SoC) to the at least two leads and coupling a portable power source ($V_{batt}$) to the SoC. The method includes measuring a difference in resistance between the at least two leads by the SoC when the at least two electrodes are attached to the body. The method includes utilizing the difference in resistance by the SoC to enable the portable power source to activate the wireless sensor device.

BRIEF DESCRIPTION OF THE DRAWINGS

The accompanying drawings illustrate several embodiments of the invention and, together with the description, serve to explain the principles of the invention. One of ordinary skill in the art readily recognizes that the particular embodiments illustrated in the drawings are merely exemplary, and are not intended to limit the scope of the present invention.

FIG. 4 illustrates the first circuit diagram after the wireless sensor device is turned on.

FIG. 7 illustrates the second circuit diagram after the wireless sensor device is turned on.

DETAILED DESCRIPTION

The present invention relates generally to wireless sensor devices, and more particularly, to a system and method for powering these wireless sensor devices. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

Figure 1:
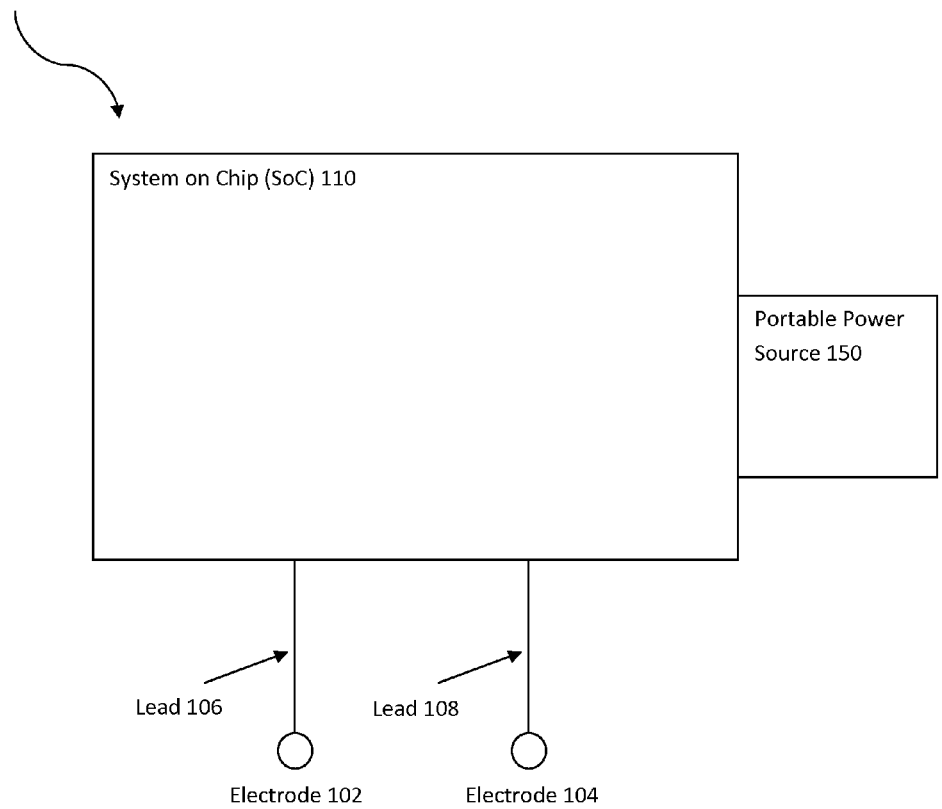
FIG. 1 illustrates a wireless sensor device in accordance with an embodiment.

FIG. 1 illustrates a wireless sensor device 100 in accordance with an embodiment. The wireless sensor device 100 includes a differential electrode pair 102-104 configured to be attached to a body, two leads 106-108 coupled to the differential electrode pair 102-104, a system on chip (SoC) 110 coupled to the two leads 106-108, and a portable power source ($V_{batt}$) 150 coupled to the SoC 110. When the two electrodes 102-104 are attached to the body, a difference in resistance is measured between the two leads 106-108 by the SoC 110. This difference in resistance is then utilized by the SoC 110 to provide power from the portable power source ($V_{batt}$) 150 to the wireless sensor device 100. To describe the features of the invention in more detail, refer now to the following description in conjunction with the following figures.

Figure 2:
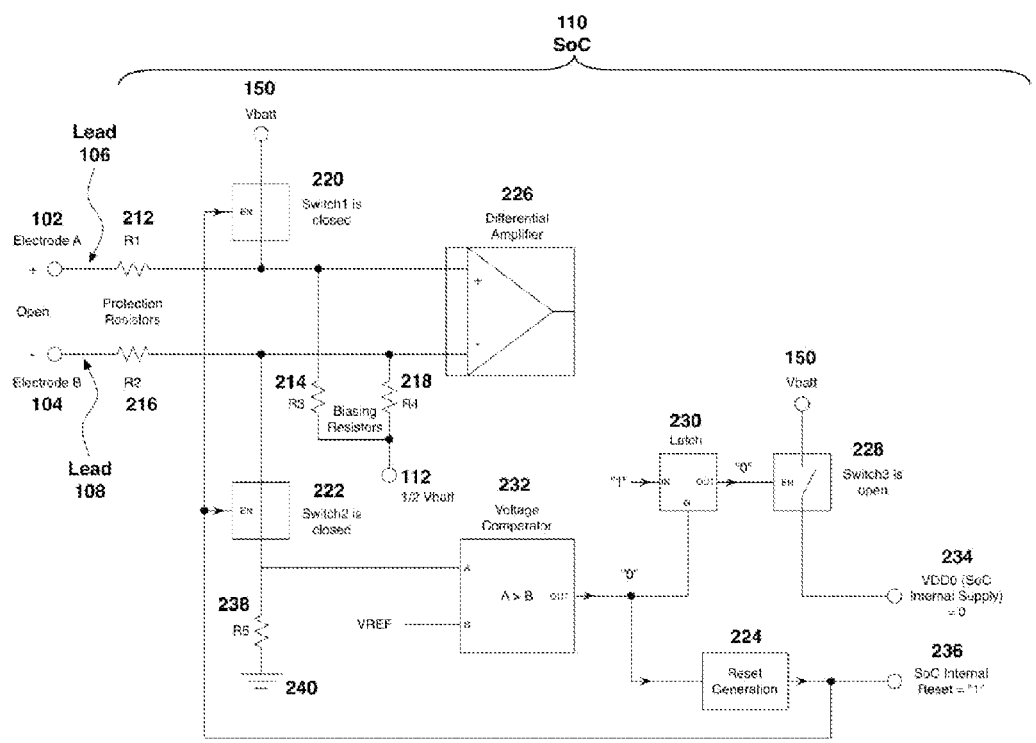
FIG. 2 illustrates an embodiment of a first circuit diagram of the wireless sensor device.

FIG. 2 illustrates an embodiment of a first circuit diagram of the wireless sensor device 100. The wireless sensor device 100 includes the differential electrode pair 102-104, wherein a first lead 106 is coupled to the positive electrode 102 and a second lead 108 is coupled to the negative electrode 104. The SoC 110 is coupled to the first and second leads 106-108, and a portable power source ($V_{batt}$) 150 is coupled to the SoC 110. One of ordinary skill in the art readily recognizes that a system and method in accordance with the present invention may utilize various implementations of the SoC 110 and that would be within the spirit and scope of the present invention.

In one embodiment, a filter is placed between the leads 106-108 and the SoC 110 to filter the input signal. One of ordinary skill in the art readily recognizes that the filter can be represented by a variety of types including but not limited to high pass, low pass, bandpass, bandreject, allpass, or any combination of passive and active components and that would be within the spirit and scope of the present invention. The filter may be coupled to the SoC 110 or be located within the SoC 110 without altering the scope of the present invention.

In one embodiment, the SoC 110 includes a first protection resistor 212 and a first biasing resistor 214 which are both coupled to the first lead 106. The SoC 110 also includes a second protection resistor 216 and a second biasing resistor 218 which are both coupled to the second lead 108. The first protection resistor 212 and the first biasing resistor 214 are both coupled to a positive input of a differential amplifier 226. The second protection resistor 216 and the second biasing resistor 218 are both coupled to a negative input of the differential amplifier 226. The first and second biasing resistors 214 and 218 are also coupled to a voltage bias (½ Vbatt) 112. One of ordinary skill in the art readily recognizes that the voltage bias 112 may be one half the portable power source ($V_{batt}$) 150 or may be any reference voltage that will bias the input of the differential amplifier 226 properly and that would be within the spirit and scope of the present invention.

In this embodiment, the first switch 220 is coupled to the first lead 106, to a portable power source 150, and to a reset generation logic 224. The second switch 222 is coupled to the second lead 108, to an input A of a voltage comparator 232, and to a reset generation logic 224. A resistor 238 is coupled to the input A of the voltage comparator 232 and to a ground 240. A reference voltage ($V_{ref}$) is coupled to an input B of the voltage comparator 232. The reset generation logic 224 is coupled between an output of the voltage comparator 232 and an internal reset pin 236. A latch logic 230 is coupled between the output of the voltage comparator 232 and a third switch 228. The third switch 228 is also coupled between the portable power source ($V_{batt}$) 150 and a SoC internal power supply (VDD0) 234.

In this embodiment, the negative input of the differential amplifier 226 is coupled to the second lead 108. The portable power source ($V_{batt}$) 150 is coupled to the first switch 220 and thus in turn to the first lead 106, and is also coupled to the third switch 228. The positive input of the differential amplifier 226 is coupled to the first lead 106.

In FIG. 2, before the differential electrode pair 102-104 is attached to a body, the first and second switches 220-222 are both in a closed configuration, the third switch 228 is in an open configuration and there is a high resistance between the differential electrode pair 102-104. One of ordinary skill in the art readily recognizes that the high resistance can be a variety of resistances including but not limited to greater than 1 mega-ohm and that would be within the spirit and scope of the present invention. The latch logic 230 and the reset generation logic 224 have been reset such that the SoC internal power supply (VDD0) 234 is disabled and the internal reset pin 236 is asserted.

In this configuration, the first lead 106 of the wireless sensor device 100 is pulled high by the portable power source ($V_{batt}$) 150 and the second lead 108 of the wireless sensor device 100 is pulled low. Therefore, the sensing voltage provided to the input A of the voltage comparator 232 is less than the reference voltage ($V_{ref}$) provided to the input B of the voltage comparator 232. Accordingly, the portable power source ($V_{batt}$) 150 is disengaged from the SoC internal power supply (VDD0) 234 and the wireless sensor device 100 is in an off configuration.

Figure 3:
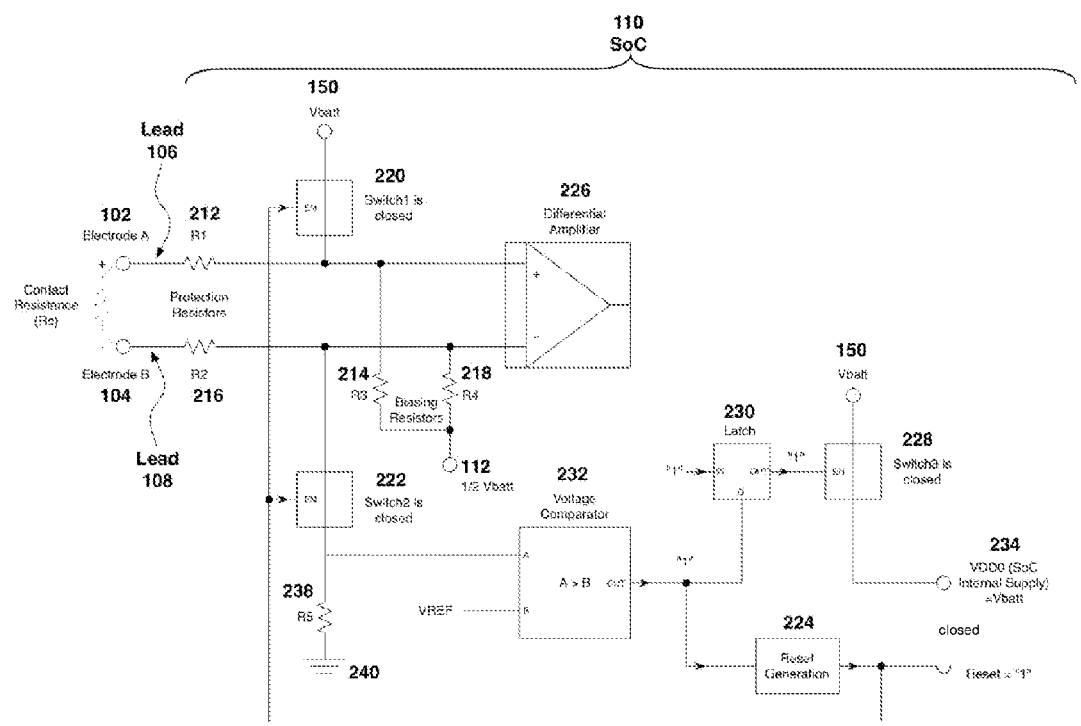
FIG. 3 illustrates the operation of the first circuit diagram when the wireless sensor device is attached to the body.

FIG. 3 illustrates the operation of the first circuit diagram when the wireless sensor device 100 is attached to the body. A contact resistance ($R_c$) of the body is provided between the differential electrode pair 102-104. The contact resistance ($R_c$) is measured by the SoC 110. Accordingly, by the introduction of the contact resistance ($R_c$), a sensing voltage at the input A of the voltage comparator 232 will be greater than the reference voltage ($V_{ref}$) that is at the input B of the voltage comparator 232.

One of ordinary skill in the art readily recognizes that a system and method in accordance with the present invention may utilize various methodologies to attach the wireless sensor device 100 in good contact to the body including but not limited to using a hydrogel and adhesive system and that would be within the spirit and scope of the present invention.

It should also be understood that the wireless sensor device 100 must be carefully designed to measure a contact resistance ($R_c$) that is within a predetermined range to provide a sensing voltage that is greater than the reference voltage ($V_{ref}$). Accordingly, the sensing voltage enables the voltage comparator 232 which in turn enables the latch logic 230. The enabling of the latch logic 230 in turn closes the third switch 228. As a result, the SoC internal power supply (VDD0) 234 is coupled to the portable power source ($V_{batt}$) 150 via the third switch 228 which begins the power-on sequence of the SoC 110.

Figure 4:
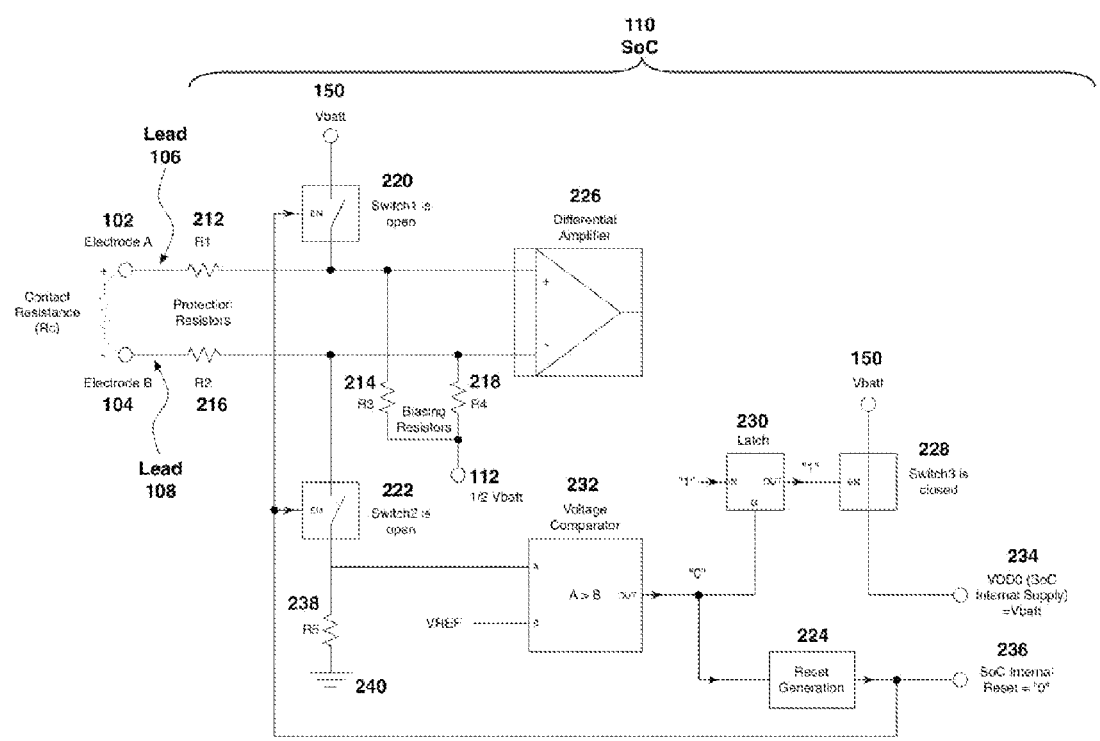

In one embodiment, after a delay lasting a predetermined time period including but not limited to a range of 1 microsecond to 1 millisecond, the wireless sensor device 100 is turned on. FIG. 4 illustrates the first circuit diagram after the wireless sensor device 100 is turned on. After the predetermined time period, the reset generation logic 224 de-asserts the internal reset pin 236 to allow the wireless sensor device 100 to turn on. Additionally, both the first switch 220 and the second switch 222 move to an open configuration which completes the power-on sequence of the SoC 110.

One of ordinary skill in the art readily recognizes that a system and method in accordance with the present invention may utilize various design considerations for the first and second protection resistors 212 and 216, first and second biasing resistors 214 and 218, contact resistance ($R_c$), and reference voltage ($V_{ref}$) and that would be within the spirit and scope of the present invention. In one embodiment, the first and second protection resistors 212 and 216 are 100 kilo-ohm (Kohm) and the contact resistance ($R_c$) is in the range of 10-800 Kohm if there is good body contact. In one embodiment, the first and second biasing resistors 214 and 218 are large, including but not limited to greater than or equal to 1 mega-ohm, to allow a maximum input swing for the differential amplifier 226.

In one embodiment, the voltage comparator 232 includes a transistor and its load impedance. In this embodiment, $V_{ref}$ is the implied turn-on or threshold voltage of the transistor. In another embodiment, the biasing resistors 214 and 218 include switches in series that enable/disable the coupling between the voltage bias 112 and the leads 106 and 108.

One of ordinary skill in the art readily recognizes that a variety of the circuit components of the present invention may be interchanged in a variety of ways including but not limited to replacing or adding to any of the resistors with impedances such as capacitors and/or inductors, and adding switches in series or in parallel to any of the circuit components in order to enable/disable a particular path at a given state of operation without altering functionality and that would be within the spirit and scope of the present invention.

Figure 5:
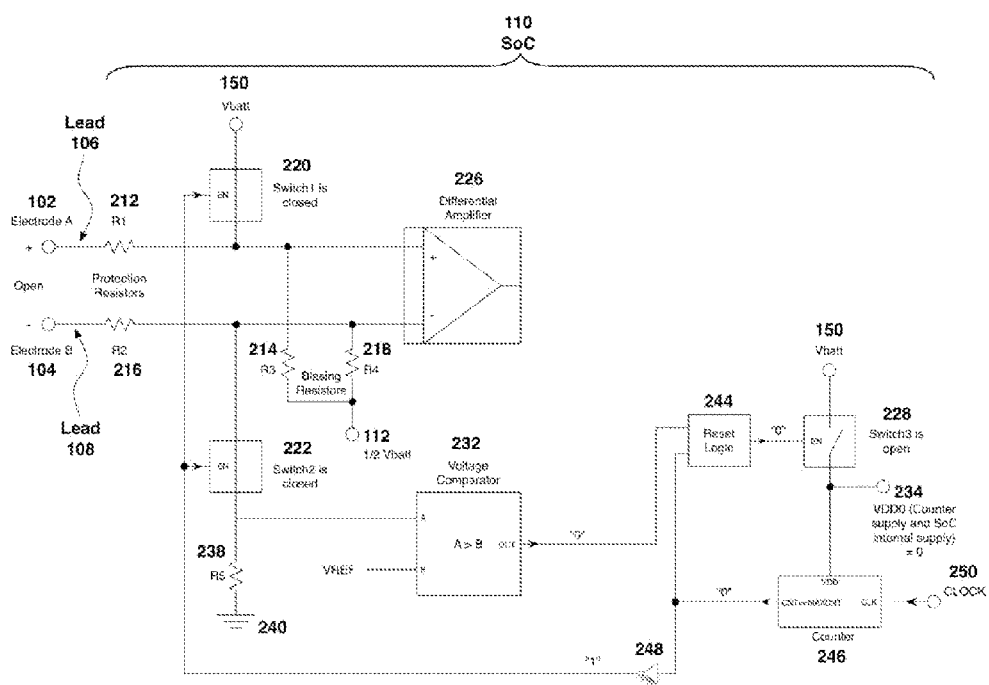
FIG. 5 illustrates an embodiment of a second circuit diagram of the wireless sensor device.

FIG. 5 illustrates an embodiment of a second circuit diagram of the wireless sensor device 100. In the second circuit diagram of FIG. 5, the wireless sensor device 100 includes the same components as the first circuit diagram of FIG. 2 except that the reset generation logic 224, the latch 230, and the internal reset pin 236 are replaced with a reset logic 244, a counter block 246, an inverter 248, and a clock input 250. In the second circuit diagram of FIG. 5, the SoC internal power supply (VDD0) 234 also serves as a counter power supply 234 for the counter block 246.

In one embodiment, the reset logic 244 gives a low output level when both the voltage comparator 232 output and the counter block 246 output are low. In another embodiment, the reset logic 244 gives a high output level when either or both of the voltage comparator 232 output and the counter block 246 output are high. When the SoC 110 is not connected to the body, the counter block 246 and the reset logic 244 are reset which results in a reset logic 244 output that is low. As a result, the third switch 228 is in an open configuration resulting in the counter power supply 234 to be low which maintains the counter block 246 output to be low. Accordingly, circuit state is maintained until contact is made with the body.

Figure 6:
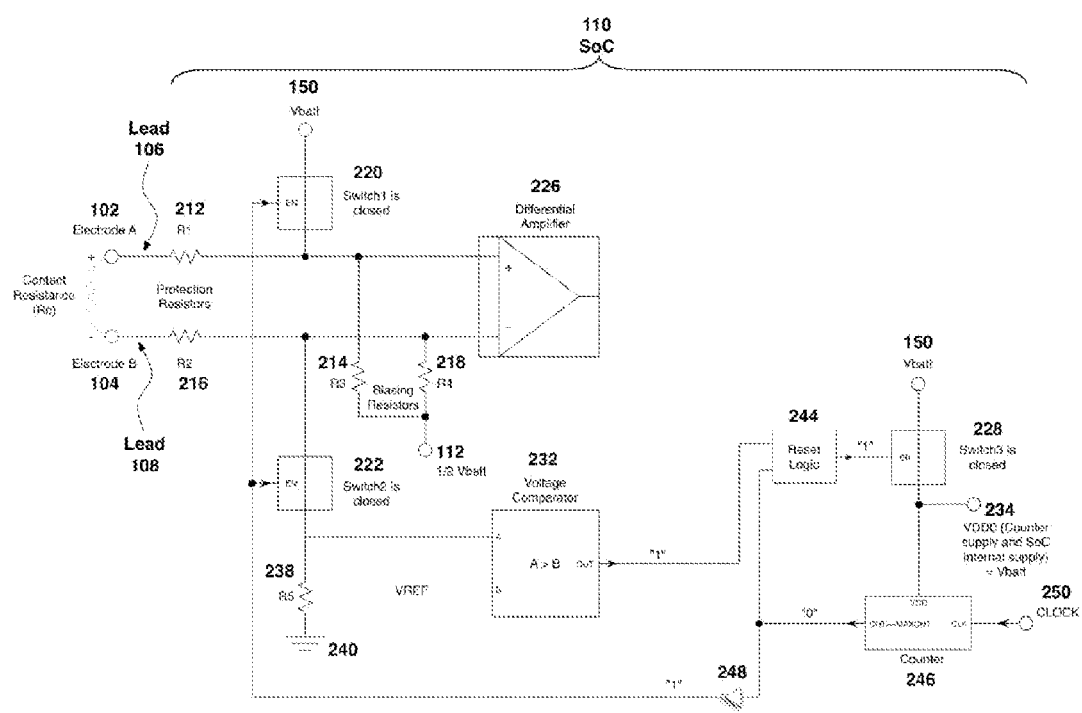
FIG. 6 illustrates the operation of the second circuit diagram when the wireless sensor device is attached to the body.
Figure 7:
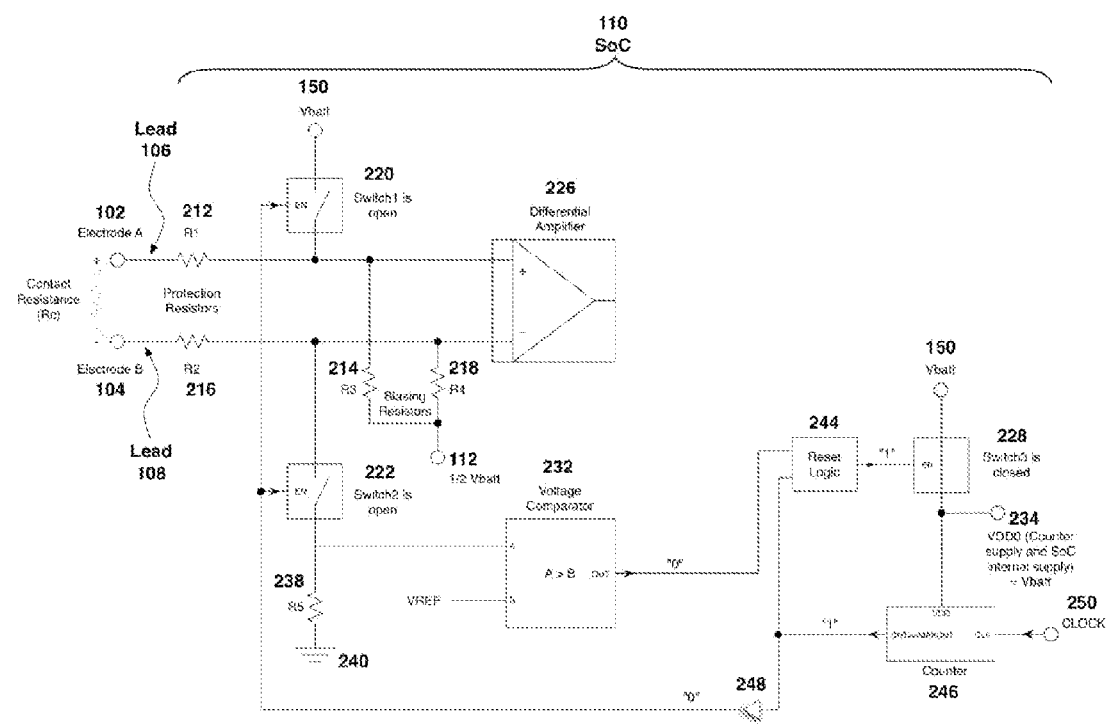

FIG. 6 illustrates the operation of the second circuit diagram when the wireless sensor device 100 is attached to the body. A contact resistance ($R_c$) is provided between the differential electrode pair 102-104. The contact resistance ($R_c$) is measured by the SoC 110. Accordingly, by the introduction of the contact resistance ($R_c$), a sensing voltage at the input A of the voltage comparator 232 will be greater than the reference voltage ($V_{ref}$) that is at the input B of the voltage comparator 232.

This in turn causes the voltage comparator 232 to have a logical high output level which transitions the reset logic 244 to a logical high output level. As a result, the third switch 228 moves to a closed configuration, forcing the counter power supply 234 to increase to $V_{batt}$ and track the portable power source 150. The counter block 246 begins to count clock cycles provided by the clock input 250. If the body contact is maintained for the amount of time it takes the counter block 246 to get to a maximum count (MAXCNT), then the counter block 246 transitions to a logical high output level which maintains the reset logic 244 output at a logical high level, causes the inverter 248 to go to a logical low level, and disables the first and second switches 220-222.

After the counter block 246 transitions to a logical high output level causing the SoC to be in an "on" state, the wireless sensor device 100 is turned on. FIG. 4 illustrates the second circuit diagram after the wireless sensor device 100 is turned on.

As above described, the system and method in accordance with the present invention allow for automatically self-powering a wireless sensor device using a contact sensing power switch. This eliminates the need for costly and burdensome recharging techniques of the wireless sensor device. The wireless sensor device is powered by implementing a hydrogel, electrode, and lead circuit system that detects and measures a difference in resistance before and after electrodes are attached in good contact to the body to couple a SoC internal power supply to a portable power source which in turn provides power to the wireless sensor device.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A wireless sensor device comprising:
   at least two electrodes configured to be attached to a body;
   at least two leads coupled to the at least two electrodes;
   a system on chip (SoC) coupled to the at least two leads, wherein the SoC includes a reset generation logic coupled to both a voltage comparator and an internal reset pin and further includes a latch logic coupled to both an output of the voltage comparator and a SoC internal power supply; and
   a portable power source ($V_{batt}$) coupled to the SoC, wherein when the latch logic is enabled by the voltage comparator, the SoC internal power supply is coupled to the portable power source;
   wherein when the at least two electrodes are attached to the body, a difference in resistance is measured between the at least two leads by the SoC using the voltage comparator, wherein after the latch logic is enabled and a predetermined time period occurs, the reset generation logic de-asserts the internal reset in to allow the wireless sensor device to turn on.

2. The wireless sensor device of claim 1, wherein the SoC further includes a voltage comparator, wherein one of the at least two leads is coupled to a first voltage input of the voltage comparator and a reference voltage is coupled to a second voltage input of the voltage comparator, wherein when a sensing voltage provided to the first voltage input is less than the reference voltage the wireless sensor device is in a first state and when the sensing voltage provided to the first voltage input is greater than the reference voltage the wireless sensor device is in a second state, wherein determination of one of the first and second states enables the portable power source to activate the wireless sensor device.

3. The wireless sensor device of claim 2, wherein after the at least two electrodes are attached to the body and a contact resistance ($R_c$) is measured by the SoC, power is provided to the wireless sensor device when the wireless sensor device is in one of the first and second states.

4. The wireless sensor device of claim 2, wherein the SoC further includes a reset logic coupled to an output of the voltage comparator and a SoC internal power supply (VDD0) coupled to the reset logic, wherein when the reset logic is enabled by the voltage comparator, the SoC internal power supply is coupled to the portable power source.

5. The wireless sensor device of claim 4, wherein the SoC further includes a counter block coupled to the reset logic and a clock input coupled to the counter block, wherein after the reset logic is enabled and a maximum count is achieved by the counter block, the counter block transitions to a logical high output level to allow the wireless sensor device to turn on.

6. The wireless sensor device of claim 1, wherein when the latch logic and the reset generation logic are reset, the SoC internal power supply is disabled and the internal reset pin is asserted to turn off the wireless sensor device.

7. The wireless sensor device of claim 1, wherein the SoC further includes a first protection resistor ($R_1$) and a first biasing resistor ($R_3$) which are both coupled to one of the at least two leads, a second protection resistor ($R_2$) and a second biasing resistor ($R_4$) which are both coupled to another of the at least two leads, and a differential amplifier coupled to the at least two leads, wherein the differential amplifier provides a bias current ($I_{bias}$), wherein the first and second biasing resistors ($R_3$ and $R_4$) have a resistance and the differential amplifier has a bias current ($I_{bias}$) to allow a maximum input swing for the differential amplifier.

8. The wireless sensor device of claim 1, wherein the at least two electrodes are configured to be attached to the body using a hydrogel.

9. A method for powering a wireless sensor device, the method comprising:
   attaching at least two electrodes to a body;
   coupling at least two leads to the at least two electrodes;
   coupling a system on chip (SoC) to the at least two leads, wherein the SoC includes a reset generation logic coupled to both a voltage comparator and an internal reset in and further includes a latch logic coupled to both an output of the voltage comparator and a SoC internal power supply;

coupling a portable power source ($V_{batt}$) to the SoC, wherein when the latch logic is enabled by the voltage comparator, the SoC internal power supply is coupled to the portable power source;

measuring a difference in resistance between the at least two leads by the SoC using the voltage comparator when the at least two electrodes are attached to the body, wherein after the latch logic is enabled and a predetermined time period occurs, the reset generation logic de-asserts the internal reset in to allow the wireless sensor device to turn on.

10. The method of claim 9, wherein the SoC includes a voltage comparator, the method further comprising:

coupling one of the at least two leads to a first voltage input of the voltage comparator; and coupling a reference voltage to a second voltage input of the voltage comparator;

wherein when a sensing voltage provided to the first voltage input is less than the reference voltage the wireless sensor device is in a first state and when the sensing voltage provided to the first voltage input is greater than the reference voltage the device is in a second state;

wherein determination of one of the first and second states enables the portable power source to activate the wireless sensor device.

11. The method of claim 10, further comprising:

measuring a contact resistance ($R_c$) by the SoC after attaching the at least two electrodes to the body; and providing power to the wireless sensor device when the wireless sensor device is in one of the first and second states.

12. The method of claim 9, wherein when the latch logic and the reset generation logic are reset, the SoC internal power supply is disabled and the internal reset pin is asserted to turn off the wireless sensor device.

13. The method of claim 9, wherein the SoC further includes a first protection resistor ($R_1$) and a first biasing resistor ($R_3$) which are both coupled to one of the at least two leads, a second protection resistor ($R_2$) and a second biasing resistor ($R_4$) which are both coupled to another of the at least two leads, and a differential amplifier coupled to the at least two leads, wherein the differential amplifier provides a bias current ($I_{bias}$), wherein the first and second biasing resistors ($R_3$ and $R_4$) have a large-resistance and the differential amplifier has a small bias current ($I_{bias}$) to allow a maximum input swing for the differential amplifier.

14. The method of claim 13, wherein when the sensing voltage provided to the first voltage input is less than the reference voltage, the sensing voltage is represented by the equation $0.5V_{batt} + I_{bias} \times R_4$.

15. The method of claim 13, wherein when the sensing voltage provided to the first voltage input is greater than the reference voltage, the sensing voltage is represented by the equation $0.5V_{batt} + R_4/(R_1 + R_c + R_2 + R_4) \times 0.5V_{batt}$.

16. The method of claim 9, further comprising:

configuring the at least two electrodes to be attached to the body using a hydrogel.

* * * * *